United States Patent
Sarkar et al.

(10) Patent No.: US 9,877,668 B1
(45) Date of Patent: Jan. 30, 2018

(54) ORIENTATION INVARIANT GAIT MATCHING

(71) Applicants: Sudeep Sarkar, Tampa, FL (US); Ravichandran Subramanian, Tampa, FL (US); Miguel A. Labrador, Tampa, FL (US)

(72) Inventors: Sudeep Sarkar, Tampa, FL (US); Ravichandran Subramanian, Tampa, FL (US); Miguel A. Labrador, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 238 days.

(21) Appl. No.: 14/944,701

(22) Filed: Nov. 18, 2015

Related U.S. Application Data

(60) Provisional application No. 62/082,769, filed on Nov. 21, 2014.

(51) Int. Cl.
 *A61B 5/11* (2006.01)
 *A61B 5/00* (2006.01)

(52) U.S. Cl.
 CPC ............ *A61B 5/112* (2013.01); *A61B 5/11* (2013.01); *A61B 5/1118* (2013.01); *A61B 5/6898* (2013.01)

(58) Field of Classification Search
 CPC ..... A61B 5/112; A61B 5/1123; A61B 5/1118; A61B 5/6898; G01C 22/006
 See application file for complete search history.

(56) References Cited

U.S. PATENT DOCUMENTS

| | | | |
|---|---|---|---|
| 7,421,369 B2 | 9/2008 | Clarkson | |
| 8,447,272 B2 | 5/2013 | Faith et al. | |
| (Continued) | | | |

FOREIGN PATENT DOCUMENTS

| | | |
|---|---|---|
| CA | 2764303 | 7/2012 |

OTHER PUBLICATIONS

Kobayashi et al.; "Rotation Invariant feature extraction from 3-D acceleration signals"; Jul. 12, 2011; IEEE; 2011 IEEE International Conference on Acoustics, Speech, and Signal Processing (ICASSP); pp. 3684-3687.*

(Continued)

*Primary Examiner* — John Villecco
(74) *Attorney, Agent, or Firm* — Thomas|Horstemeyer, LLP.

(57) ABSTRACT

Aspects of gait matching are described herein. In one embodiment, a method of gait matching includes identifying a gait cycle timing in a data sequence captured by an inertial sensor, splitting the data sequence into a gait cycle segment, resampling the gait cycle segment, and estimating a rotation matrix for the resampled gait cycle segment. The rotation matrix, in one embodiment, can be estimated by minimizing a root mean squared deviation between the resampled gait cycle segment and a reference gait cycle segment using the Kabsch algorithm, for example. The method further includes calculating an aligned gait cycle segment from the resampled gait cycle segment using the rotation matrix, and generating a similarity measure between the aligned gait cycle segment and the reference gait cycle segment. The Kabsch algorithm can be used to minimize error and reduce identity authentication errors.

20 Claims, 13 Drawing Sheets

(56) References Cited

U.S. PATENT DOCUMENTS

| | | | | |
|---|---|---|---|---|
| 9,265,448 | B2* | 2/2016 | Bonnet | A61B 5/1038 |
| 2005/0209536 | A1* | 9/2005 | Dariush | A61B 5/1038 |
| | | | | 600/595 |
| 2012/0065915 | A1* | 3/2012 | Hara | A61B 5/1121 |
| | | | | 702/96 |
| 2014/0142864 | A1* | 5/2014 | Spears | A61B 5/1112 |
| | | | | 702/19 |
| 2014/0156215 | A1 | 6/2014 | Eastman | |
| 2015/0112603 | A1 | 4/2015 | Zhong | |
| 2015/0272480 | A1* | 10/2015 | Senta | G01P 15/18 |
| | | | | 600/595 |
| 2015/0276793 | A1* | 10/2015 | Takenaka | G01P 15/18 |
| | | | | 73/504.03 |
| 2016/0100801 | A1* | 4/2016 | Clark | A61B 5/6807 |
| | | | | 73/865.4 |
| 2016/0192863 | A1* | 7/2016 | Zhong | A61B 5/112 |
| | | | | 600/595 |
| 2017/0095181 | A1* | 4/2017 | Hauenstein | A61B 5/6823 |
| 2017/0225033 | A1* | 8/2017 | Czaja | A63B 24/0006 |

OTHER PUBLICATIONS

Yu Zhong; Yunbin Deng, "Sensor orientation invariant mobile gait biometrics," in Biometrics (IJCB), 2014 IEEE International Joint Conference on , vol., No., pp. 1-8, Sep. 29, 2014-Oct. 2, 2014.

Kobayashi, T.; Hasida, K.; Otsu, N., "Rotation invariant feature extraction from 3-D acceleration signals," in Acoustics, Speech and Signal Processing (ICASSP), 2011 IEEE International Conference on , vol., No., pp. 3684-3687, May 22-27, 2011.

Ye Chen; Weijian Hu; Yu Yang; Jijian Hou; Zhelong Wang, "A method to calibrate installation orientation errors of inertial sensors for gait analysis," in Information and Automation (ICIA), 2014 IEEE International Conference on , vol., No., pp. 598-603, Jul. 28-30, 2014.

Subramanian, R.; Sarkar, S.; Labrador, M.; Contino, K.; Eggert, C.; Javed, O.; Jiejie Zhu; Hui Cheng, "Orientation invariant gait matching algorithm based on the Kabsch alignment," in Identity, Security and Behavior Analysis (ISBA), 2015 IEEE International Conference on, vol., No., pp. 1-8, Mar. 23-25, 2015).

Sprager, Sebastijan, and Matjaz B. Juric. "Inertial Sensor-Based Gait Recognition: A Review." Sensors 15.9 (Sep. 2015): 22089-22127.

Henpraserttae, A.; Thiemjarus, S.; Marukatat, S., "Accurate Activity Recognition Using a Mobile Phone Regardless of Device Orientation and Location," in Body Sensor Networks (BSN), 2011 International Conference on , vol., No., pp. 41-46, May 23-25, 2011.

Barthold, C.; Subbu, K.P.; Dantu, R., "Evaluation of gyroscope-embedded mobile phones," in Systems, Man, and Cybernetics (SMC), 2011 IEEE International Conference on , vol., No., pp. 1632-1638, Oct. 9-12, 2011.

Ngo, T.T; Makihara, Y; Nagahara,H; Mukaigawa, Y; Yagi, Y., "Orientation-Compensative Signal Registration for Owner Authentication Using an Accelerometer" in IEICE Transactions on Information and Systems, E97-D (3) (Mar. 2014), pp. 541-553.

Derawi, M.O.; Nickel, C.; Bours, P.; Busch, C., "Unobtrusive User-Authentication on Mobile Phones Using Biometric Gait Recognition," in Intelligent Information Hiding and Multimedia Signal Processing (IIH-MSP), 2010 Sixth International Conference on , vol., No., pp. 306-311, Oct. 15-17, 2010.

M. Derawi, P. Bours, and K. Holien. Improved cycle detection for accelerometer based gait authentication. In International Conference on Intelligent Information Hiding and Multimedia Signal Processing (IIH-MSP), pp. 312-317, Oct. 2010.

J. Frank, S. Mannor, J. Pineau, and D. Precup. Time series analysis using geometric template matching. IEEE Transactions on Pattern Analysis and Machine Intelligence, 35(3):740-754, 2013.

D. Gafurov, E. Snekkenes, and P. Bours. Improved gait recognition performance using cycle matching. In International Conference on Advanced Information Networking and Applications Workshops, pp. 836-841, 2010.

D. Gafurov, K. Helkala, and T. Søndrol. Biometric gait authentication using accelerometer sensor. Journal of computers, 1(7):51-59, Nov. 2006.

T. Iso and K. Yamazaki. Gait analyzer based on a cell phone with a single three-axis accelerometer. In ACM Conference on Human-computer interaction with mobile devices and services, pp. 141-144, Sep. 2006.

F. Juefei-Xu, C. Bhagavatula, A. Jaech, U. Prasad, and M. Savvides. Gait-id on the move: pace independent human identification using cell phone accelerometer dynamics. In IEEE International Conference on Biometrics: Theory, Applications and Systems, pp. 8-15, Sep. 2012.

W. Kabsch. A discussion of the solution for the best rotation to relate two sets of vectors. Acta Crystallographica Section A: Crystal Physics, Diffraction, Theoretical and General Crystallography, 34(5):827-828, 1978.

J. R. Kwapisz, G. M. Weiss, and S. A. Moore. Cell phonebased biometric identification. In IEEE International Conference on Biometrics: Theory Applications and Systems (BTAS), pp. 1-7, 2010.

J. Mantyjarvi, M. Lindholm, E. Vildjiounaite, S.-M. Makela, and H. Ailisto. Identifying users of portable devices from gait pattern with accelerometers. In IEEE International Conference on Acoustics, Speech, and Signal Processing. Proceedings, vol. 2, pp. 973-976, Mar. 2005.

T. T. Ngo, Y. Makihara, H. Nagahara, Y. Mukaigawa, and Y. Yagi. The largest inertial sensor-based gait database and performance evaluation of gait-based personal authentication. Pattern Recognition, 47(1):228-237, Jan. 2014.

C. Nickel, C. Busch, S. Rangarajan, and M. Mobius. Using hidden markov models for accelerometer-based biometric gait recognition. In International Colloquium on Signal Processing and its Applications, pp. 58-63, Mar. 2011.

T. Oö berg, A. Karsznia, and K. Oö berg. Basic gait parameters: reference data for normal subjects, 10-79 years of age. Journal of rehabilitation research and development, 30:210-210, 1993.

G. Pan, Y. Zhang, and Z. Wu. Accelerometer-based gait recognition via voting by signature points. Electronics letters, 45(22):1116-1118, Oct. 2009.

L. Rong, Z. Jianzhong, L. Ming, and H. Xiangfeng. A wearable acceleration sensor system for gait recognition. In IEEE Conference on Industrial Electronics and Applications, pp. 2654-2659, May 2007.

S. Sprager and D. Zazula. A cumulant-based method for gait identification using accelerometer data with principal component analysis and support vector machine. WSEAS Transactions on Signal Processing, 5(11):369-378, Nov. 2009.

Yu Zhong, Yunbin Deng, Geoffrey Meltzner—Pace Independent Mobile Gait Biometrics, IEEE BTAS Sep. 2015.

Yuting Zhang, Gang Pan, Kui Jia, Minlong Lu, Yueming Wang, and Zhaohui Wu—Accelerometer-Based Gait Recognition by Sparse Representation of Signature Points With Clusters, IEEE Transactions on Cybernetics, vol. 45, No. 9, Sep. 2015.

* cited by examiner

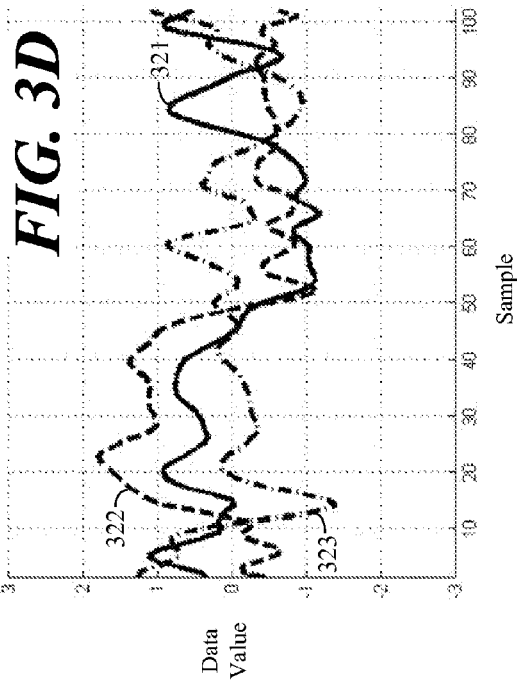
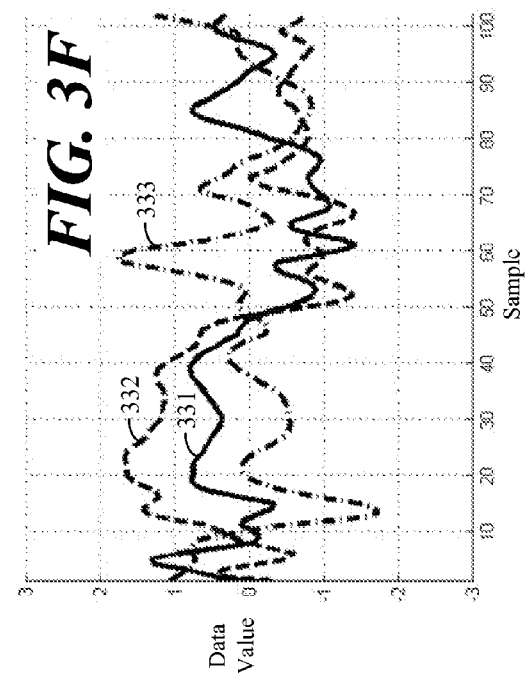
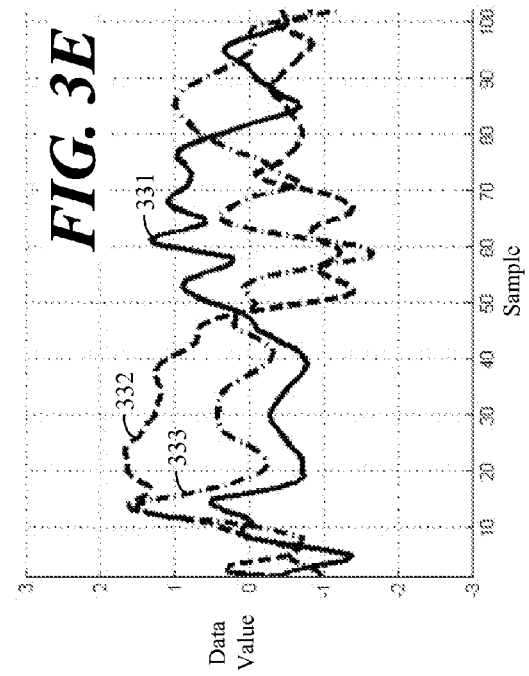

ORIENTATION INVARIANT GAIT MATCHING

CROSS-REFERENCE TO RELATED APPLICATIONS

This application claims the benefit of U.S. Provisional Application No. 62/082,769, filed Nov. 21, 2014, the entire contents of which is hereby incorporated herein by reference.

GOVERNMENT LICENSE RIGHTS

This invention was made with Government support under Contract FA8750-13-C-0265 awarded by the Air Force. The Government has certain rights in the invention.

BACKGROUND

Generally, gait is the pattern that the body frame and/or limbs of animals exhibit during movement. Most animals exhibit different gaits based on certain factors, such as speed and terrain, among others. Human gait refers to the pattern or patterns exhibited by the movement of the human body frame and/or human limbs. For example, human gait may be described in terms of bipedal forward propulsion of the human body, including alternate but repeating movements of different body segments. Different gait patterns are characterized by differences in limb movement patterns, such as differences in velocity, forces, and potential energy, as well as differences due to changes in surface contact. Thus, different human gaits are representative of the different ways that humans can move.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

FIGS. 3D-3F illustrate the effect of rotation alignment for gyroscope data according to various embodiments described herein.

DETAILED DESCRIPTION

Figure 1:
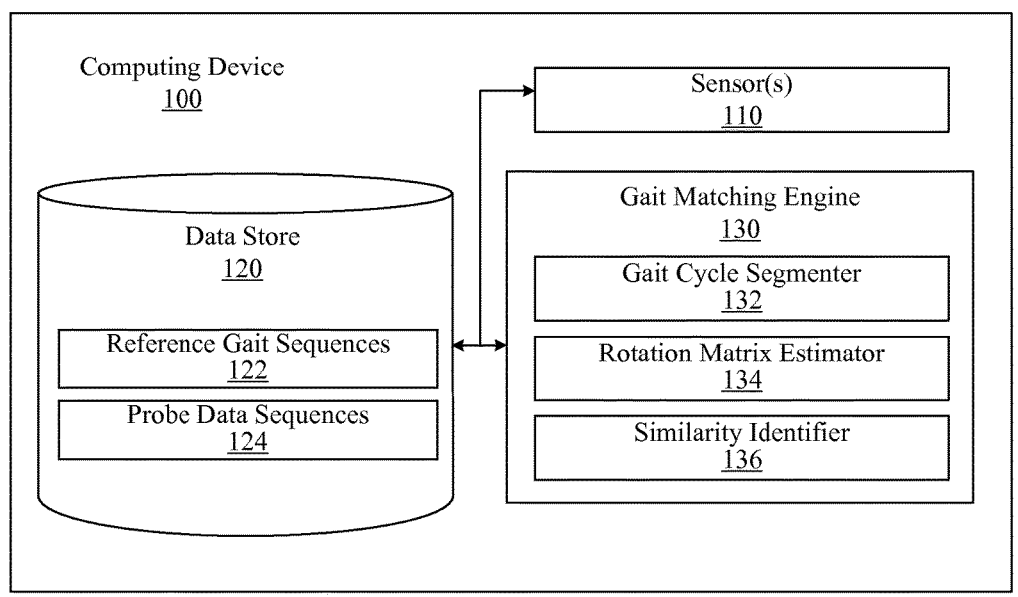
FIG. 1 illustrates an example computing device for orientation invariant gait matching according to various embodiments described herein.

Human gait is the overall pattern of bipedal locomotion of an individual. It is largely determined by an individual's body structure and behavioral patterns acquired over an extended period of time. Similar to a fingerprint, human gait can be used as a measure for identity authentication. Recently, there has been increased interest in exploring the biometric authentication potential of gait as captured through various sensors. Most of the exploration has been with the capture of gait through cameras at a distance. Using gait video captured by cameras, correct identification rates range from about 80% to 90%. Identification rates using video vary, however, based on various factors including camera view, shoe and speed changes, walking surface differences, clothing differences, etc.

With the proliferation of wearable devices having integrated inertial sensors, such as smart phones, smart watches, smart glasses, fitness bands, etc., data captured by these sensors can be used for gait-based authentication. Thus, inertial sensors in various devices, such as accelerometer and gyroscope sensors, can be relied upon to capture the dynamics of human gait. In certain applications, the data captured by these inertial sensors can achieve higher gait-based authentication accuracy, because the inertial sensors are co-located with the user. Examples of inertial sensors include accelerometer and gyroscope sensors, for example, which measure acceleration and rate of rotation, respectively, along a multi-axis (e.g., 3-axis) coordinate system. Based on the physical design of a device, the multi-axis coordinate system of the inertial sensors is defined relative to the the device.

In the context of a smart phone, for example, one or more inertial sensors can be used to capture data representative of an individual's gait. However, the phone can be placed in different orientations over time. For example, the individual may be holding the phone while texting and walking over a first period of time, and the phone may be placed in the individual's pocket over a second period of time. Because the data captured by the inertial sensors is provided as a set orientation-defined vector sequences, the data will reflect a significant change in orientation when the phone is placed into the individual's pocket as compared to when it is held in the individual's hand. Thus, gait data is likely to reflect differences in position and/or orientation, among other factors, while being captured during different activities and/or at different periods of time. Often, these differences can result in a poor match of gait data even for the same individual.

While the placement of the device on the individual can be controlled or expected to some extent (e.g., because smart phones are commonly placed in a hip pocket), it is not practical or possible to control the orientation of the device under all circumstances. Even when placed in the pocket of the individual, the device could be placed in different orientations. For accuracy in identity authentication, this difference in orientation should be accounted for in any gait-matching algorithm. One way to handle matching across different orientations is to use only the magnitude of the signal. However, this ignores gait dynamic information captured in the multi-axis coordinate data provided by inertial sensors. Error rates can be high when using the magnitudes of inertial sensor data. Frequency domain methods also appear to perform poorly when used to address the orientation issue.

According to the embodiments described herein, a new orientation invariant gait-matching algorithm is described. The algorithm includes gait cycle identification, cycle splitting, orientation alignment, and gait comparison for identity authentication. As for the orientation alignment, the Kabsch algorithm is used in some embodiments to minimize the RMS error between rotated sensor data as compared to a reference gait data. Further, a unique dataset, including variations in phone placement and/or orientation collected over a number of weeks for various subjects, was used to test the accuracy of the new algorithm described herein. Thus, the effectiveness of the algorithm is demonstrated using a dataset collected from a significant number of subjects with various device orientations. As described and shown herein, the orientation invariant gait matching algorithm described herein results in a significant reduction in identity authentication error.

Turning to the drawings, FIG. 1 illustrates an example computing device 100 for orientation invariant gait matching according to various embodiments described herein. The computing device 100 can be embodied as any type of computing or processing device or system having memory, including those embodied in the form of a desktop computer, laptop computer, tablet computer, personal digital assistant, digital camera, smart phone, wearable computing device, or other device. Examples of wearable computing devices include smart watches, wristbands, fitness bands, and wearable heads-up display computing devices, such as smart glasses, virtual-reality headsets, etc. Beyond the components described below, the computing device 100 can include other subsystems, such as wireless communications transceivers, GPS receivers, biometric sensors, speakers, displays, etc. The computing device 100 can also include one or more peripheral system or subsystem devices. In this context, the peripheral devices can include one or more input devices, output devices, sensors, etc., such as a keyboard, keypad, touch pad, touch screen, microphone, imaging device (e.g., camera), etc.

As shown in FIG. 1, the computing device 100 includes one or more sensors 110, a data store 120, and a gait matching engine 130. The sensors 110 can be embodied as one or more micro- or nano-electromechanical system (NEMS or MEMS) or other type of inertial sensor, such as accelerometer, gyroscope, orientation, or other motion sensors. The sensors 110 can provide signals representative of the orientation and/or movement of the computing device 100. These sensors can be used by the computing device 100 to track the movement and orientation of the computing device 100 over time for orientation invariant gait-matching. When the sensors 110 include accelerometer and gyroscope sensors, for example, the sensors 110 can measure acceleration and rate of rotation, respectively, along a multi-axis (e.g., 3-axis) coordinate system of the computing device 100. The multi-axis coordinate system of the inertial sensors can be defined relative to the orientation of the computing device 100, as described in further detail below with reference to FIGS. 2A and 2B, or relative to another device in which the sensors 110 are contained.

In other embodiments, the sensors 110 may be dislocated or separated from the computing device 100. For example, the sensors 110 can be contained in a wearable computing device, such as a smart watch, wristband, fitness band, smart glasses, virtual-reality headset, etc., and the data store 120 and gait matching engine 130 can be contained in a desktop computer, laptop computer, tablet computer, personal digital assistant, smart phone, or other computing device. Thus, the sensors 110 can be incorporated in a wearable device for data collection, while data storage and processing activities occur in another device. In some embodiments, the data store 120 and gait matching engine 130 can geographically separated from the sensors 110. In an embodiment where the sensors 110 are separate from the computing device 100, the data captured from the sensors 110 can be relayed to the data store 120 and/or the gait matching engine 130 using any suitable communications network(s), including the Internet, intranets, extranets, wide area networks (WANs), local area networks (LANs), wired networks, wireless networks, cable networks, satellite networks, other suitable networks, or any combinations thereof.

The data store 120, which may be embodied as any suitable type of computer-readable memory, can store reference gait sequences 122. The reference gait sequences 122, which are also referred to as gallery or reference data, are representative of signatures associated with one or more individuals. Similar to a fingerprint, each reference gait sequence 122 is associated with the unique gait of an individual and can be compared against other data sequences for identity authentication. Any given reference gait sequence 122 can be compiled or formed from one or more data sequences captured for a given individual over time. In some embodiments, the reference gait sequences can include one or more reference gait segments, each split along and representative of one gait cycle of an individual. The data store 120 can also store current, ongoing data sequences captured by the sensors 110 as the probe data sequences 124.

The gait matching engine 130 includes the gait cycle segmenter 132, the rotation matrix estimator 134, and the similarity identifier 136. In operation, while the computing device 100 is being moved, the sensors 110 capture one or more data sequences representative of the movement (e.g., acceleration and/or rate of rotation) of the computing device 100, sampled over time. In various embodiments, the sensors 110 can provide the data sequences at any suitable sample rate of the movement. Further, the sensors 110 can capture and provide vector data sequences representative of the movement of the computing device 100 along a multi-axis coordinate system. In that context, a vector data sequence can include multiple, respective data sequences, each associated with or aligned to a geometric axis of the computing device 100 as described in further detail below. The data sequences can be stored in the data store 120 as the probe data sequences 124.

For identity authentication, two data sequences are provided as inputs to the gait matching engine 130, including a reference gait sequence or segment from the reference gait sequences 122 and a data sequence from the sensors 110 (and/or from the probe data sequences 124). In one embodiment, the data sequence from the sensors 110 is embodied as a three-dimensional acceleration vector sequence (with or without gravity having been removed), $\{\ddot{x}(i)|i=0:n-1\}$, and/or a three-dimensional gyroscope vector sequence, $\{\dot{\theta}(i)|i=0:n-1\}$.

Figure 2A:
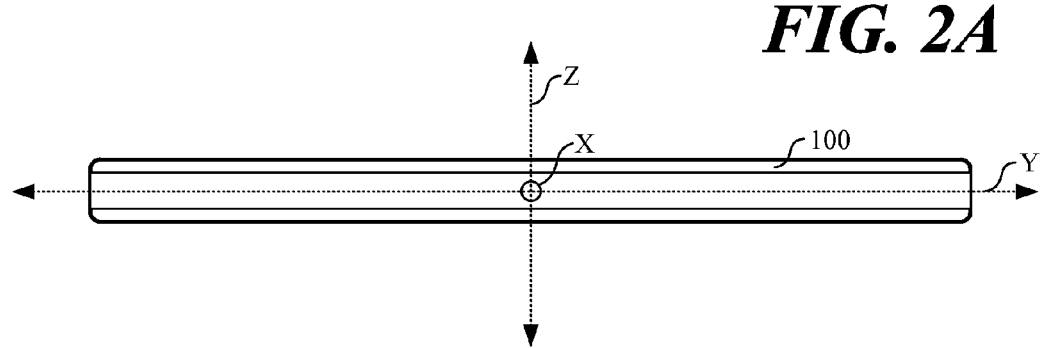
FIGS. 2A and 2B illustrate three example axes of a computing device according to various embodiments described herein.
Figure 2B:
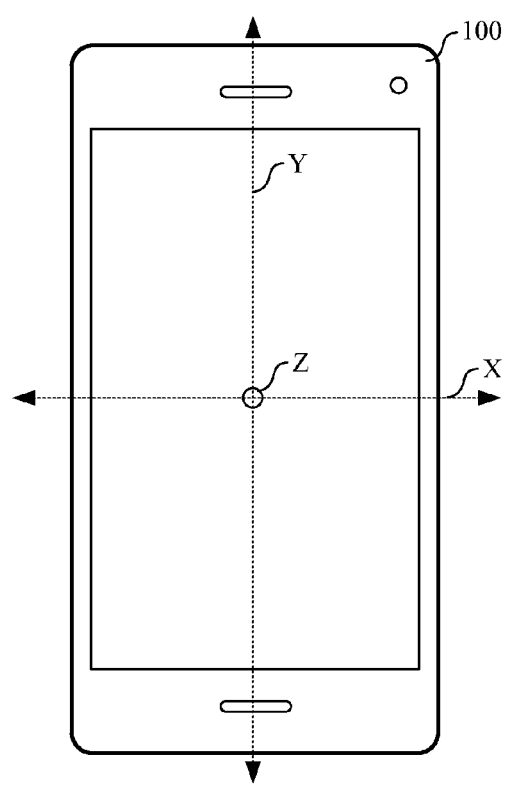

With regard to the multi-dimensional nature of the data sequences captured by the sensors 110, FIGS. 2A and 2B illustrate three example geometrical axes of the computing device 100. As shown in FIGS. 2A and 2B, three example axes, X, Y, and Z, are shown for the computing device 100. The Z axis extends perpendicularly outward from the face of the computing device 100, the X axis extends laterally across the computing device 100, and the Y axis extends longitudinally along the computing device 100. By physical design, the sensors 110 are oriented within the computing device 100 to capture data sequences aligned with the X, Y, and Z axes. Thus, the three-dimensional acceleration and/or gyroscope data sequences captured by the sensors 110 are vector data sequences including X, Y, and Z components that are reference-aligned to the X, Y, and Z axes in FIGS. 2A and 2B.

According to aspects of the embodiments, the data sequence from the sensors 110 is a periodic signal that is split into gait cycles and resampled to arrive at sequences of fixed lengths. In that context, the gait cycle segmenter 132 is configured to split the data sequence from the sensors 110 into gait cycle segments. In one embodiment, to split the signal into individual gait cycles segments, the gait cycle segmenter 132 estimates a period of the data sequence from the sensors 110 based on the circular auto-correlation function given by:

$$r(k) = \sum_{i=0}^{n-1} \ddot{x}^T(i)\ddot{x}((i-k) \bmod n)$$

for k=0: n−1. The auto-correlation function signal is periodic, but with reduced noise because the summation reduces noise levels. This makes it easier to detect peaks that correspond to the periodicity in the data sequence. To find the peak, the gait cycle segmenter 132 first detects all local maxima points (e.g., points in the signal such as r(k)>r(k+1) and r(k)>r(k−1)). Sub-dominant peaks within a sliding window of ±0.2 second length can be eliminated. In one embodiment, the period estimate is the location of the peak closest to one second, although other timings can be used. The estimate of one second is reasonable given that the typical cadence for human gait is about 1.8 to 2.3 steps per second, which relates to a gait period of about 0.87 to 1.11 seconds per cycle. In other embodiments, the period of the data sequence can be estimated without using an auto-correlation function, such as using frequency analysis or other suitable methods.

Using the estimate of the gait period, the gait cycle segmenter 132 is configured to split the original data sequence from the sensors 110, $\ddot{x}$ or $\dot{\theta}$, into gait cycle segments by eliminating sub-dominant peaks in the magnitude of the $\ddot{x}$ signal within a ±20% period length window. Each remaining peak is paired off with a succeeding peak that lies within a ±20% window centered an estimated period away from it, to form a gait cycle. If no matching peak is found in the window, no cycle is formed.

Typically, this results in overlapping cycles that correspond to starting with the left or right foot. The resulting cycles are of varying time duration and hence contain a different number of samples. To facilitate the distance computation, each gait cycle is re-sampled by linear interpolation to produce a number of samples m. Among the embodiments, m can be 102 samples or another suitable number. Thus, the gait cycle segmenter 132 is further configured to resample the gait cycle segments into resampled gait cycle segments, each having a fixed length. These re-sampled and segmented measurements can be denoted by 3×m matrices $\hat{\ddot{x}} = [\hat{\ddot{x}}(0), \ldots, \hat{\ddot{x}}(m-1)]$ and $\hat{\dot{\theta}} = [\hat{\dot{\theta}}(0), \ldots, \hat{\dot{\theta}}(m-1)]$ corresponding to the accelerometer and gyroscope measurements, where each column is a measurement.

Before two signals, $\hat{\ddot{x}}_1$ and $\hat{\ddot{x}}_2$ (or $\hat{\dot{\theta}}_1$ and $\hat{\dot{\theta}}_2$) (e.g., a resampled gait cycle segment and a reference gait cycle segment) are compared for identity authentication, the rotation matrix estimator 134 is configured to estimate a rotation matrix R for one or more resampled gait cycle segments by minimizing a deviation between any given resampled gait cycle segment and the reference gait cycle segment. A rotation matrix R can be estimated for each resampled gait cycle segment or for a group of resampled gait cycle segments. For a three-dimensional vector data sequence, the rotation matrix estimator 134 generates an appropriate 3 by 3 rotation matrix R. The rotation matrix can be estimated by minimizing the $L^2$ (Frobenius) norm by:

$$\hat{R} = \mathrm{argmin}_R \left\| \hat{\ddot{x}}_1 - R\hat{\ddot{x}}_2 \right\|_2. \qquad (1)$$

This approach is similar to minimizing the trace $(\hat{\ddot{x}}_1 - R\hat{\ddot{x}}_2)^T(\hat{\ddot{x}}_1 - R\hat{\ddot{x}}_2)$. A similar problem was solved by Kabsch in the context of crystallography. The solution can be constructed from the singular value decomposition (SVD) of the 3×3 matrix $\hat{\ddot{x}}_1 \hat{\ddot{x}}_2^T$ given by $U\Lambda V^T$. The ambiguity of the rotation matrix in terms of a right-handed coordinate system can be resolved by estimating the sign using s=sign(det($VU^T$)). Using this, the optimal rotation matrix is given by $$\hat{R} = V \begin{pmatrix} 1 & 0 & 0 \\ 0 & 1 & 0 \\ 0 & 0 & s \end{pmatrix} U^T. \qquad (2)$$

Figure 3A:
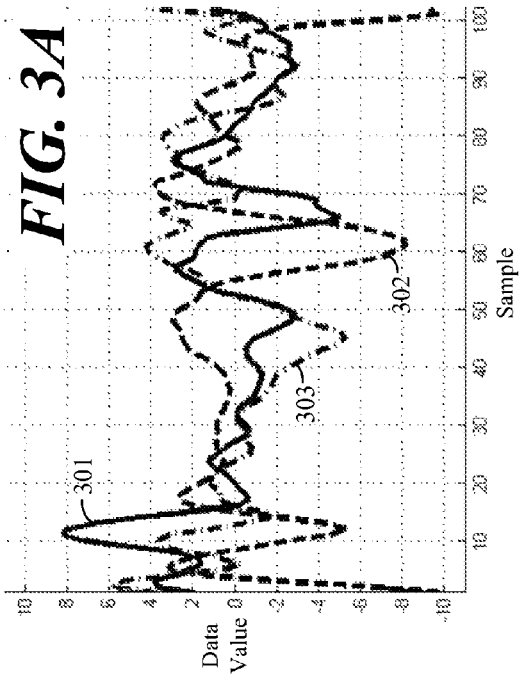
FIGS. 3A-3C illustrate the effect of rotation alignment for accelerometer data according to various embodiments described herein.
Figure 3C:
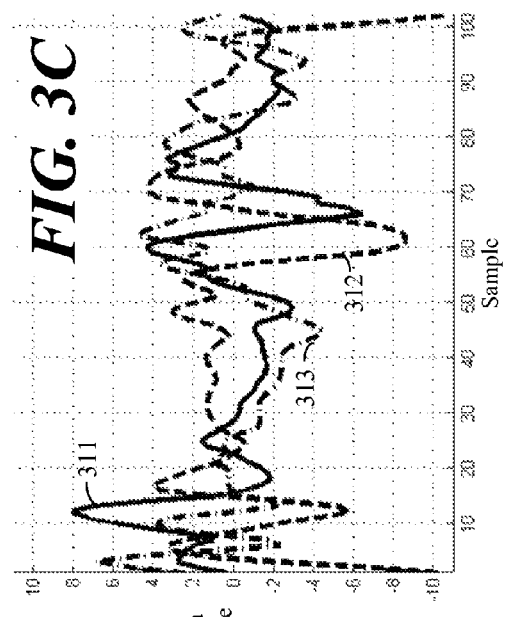
Figure 3B:
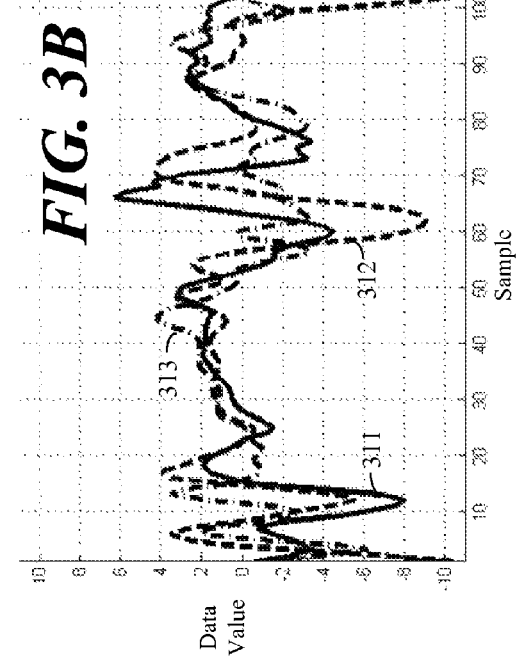

After the rotation matrix R is estimated, the gait matching engine 130 is configured to calculate an aligned gait cycle segment from the resampled gait cycle segment using the rotation matrix R. For example, an illustration of the effect of rotation alignment is shown in FIGS. 3A-3C. Particularly, FIGS. 3A-3C illustrate the effect of rotation alignment for accelerometer data. In FIG. 3A, lines 301, 302, and 303 are example gallery or reference sensor data along the X, Y, and Z directions, respectively. In FIGS. 3B and 3C, lines 311, 312, and 313 are accelerometer data from the sensors 110 along the X, Y, and Z directions, respectively. FIG. 3B shows the original data from the sensors 110. Note that the X (311) and Z (313) signals are opposite in sign between FIGS. 3A and 3B/3C. This indicates that the computing device 100 is flipped about its Y axis. FIG. 3C shows the sensor data after alignment in orientation with the reference sensor data in FIG. 3A.

FIGS. 3D-3F illustrate the effect of rotation alignment for gyroscope data. In FIG. 3D, lines 321, 322, and 323 are example gallery or reference sensor data along the X, Y, and Z directions, respectively. In FIGS. 3E and 3F, lines 331, 332, and 333 are gyroscope data from the sensors 110 along the X, Y, and Z directions, respectively. FIG. 3E shows the original data from the sensors 110. FIG. 3F shows the sensor data after alignment in orientation with the reference sensor data in FIG. 3D.

The similarity identifier 136 is configured to generate a similarity measure between the aligned gait cycle segment and the reference gait cycle segment. For example, reference gait cycle segment and the rotation-aligned gait cycle segment can be compared using the Tanimoto similarity measure. The Tanimoto similarity between the reference signal $\hat{\ddot{x}}_1$ and aligned signal $\hat{\ddot{x}}_2$ can be computed as:

$$T(\hat{X}_1, \hat{X}_2) = \frac{\hat{X}_1 \circ \hat{X}_2}{\hat{X}_1 \circ \hat{X}_1 + \hat{X}_2 \circ \hat{X}_2 - \hat{X}_1 \circ \hat{X}_2}, \quad (3)$$

where the operation A∘B denotes the sum of the entry wise multiplication of the matrices, i.e. $\Sigma_i \Sigma_j A_{ij} B_{ij}$. For signals that are similar, the value of this measure will be close to 1 and less if they are dissimilar. In other words, the value of this measure can be used for identity authentication, similar to the way that an individual's fingerprint can serve as a unique identifier.

Results on three different datasets are presented below. The results are presented on (i) the PDA dataset collected at the University of South Florida (USF) from 101 subjects with variations in phone placement, days, and activities; (ii) the McGill dataset from 20 subjects with data collected on different days and orientation variations; and (iii) the OU-ISIR dataset from 745 subjects without orientation variation. The OU-ISIR dataset is a current standard in gait recognition from inertial sensors.

For the PDA dataset, data was collected from a total of 101 subjects. A custom Java application was used to collect various sensor data on Google Nexus 5 phones. The data was collected at a nominal rate of 100 Hz and time-stamped from each sensor independently. The physical and virtual sensors used were: linear acceleration, gyroscope, gravity, total acceleration (gravity+linear acceleration), magnetic field, sound level, orientation (pitch, roll, and yaw), rotation vector, and rotation matrix. The PDA dataset includes variation in phone placement for various activities performed by the subjects. It also includes data collected on different days from the same subject. During each collection session, six gait related activities as shown in Table 1 were collected for each subject. In Table 1, six gait activities are shown, having activity IDs 13-18. The phone location is where the phone was placed when the subject was not using the phone. Phone Action is the mode of phone usage by the subject, if any.

TABLE 1

Collected Gait Related Activity Data

| Activity ID | Phone location | Phone action |
|---|---|---|
| 13 | Pocket | NONE |
| 14 | Pocket | Talk |
| 15 | Pocket | Text |
| 16 | Holster | NONE |
| 17 | Holster | Talk |
| 18 | Holster | Text |

Figure 4:
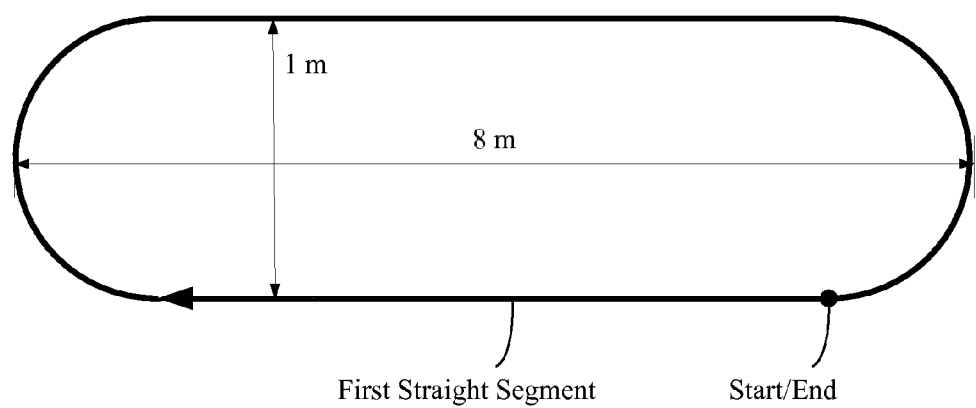
FIG. 4 illustrates a walking path used by subjects during data collection for various activities according to embodiments described herein.
Figure 5A:
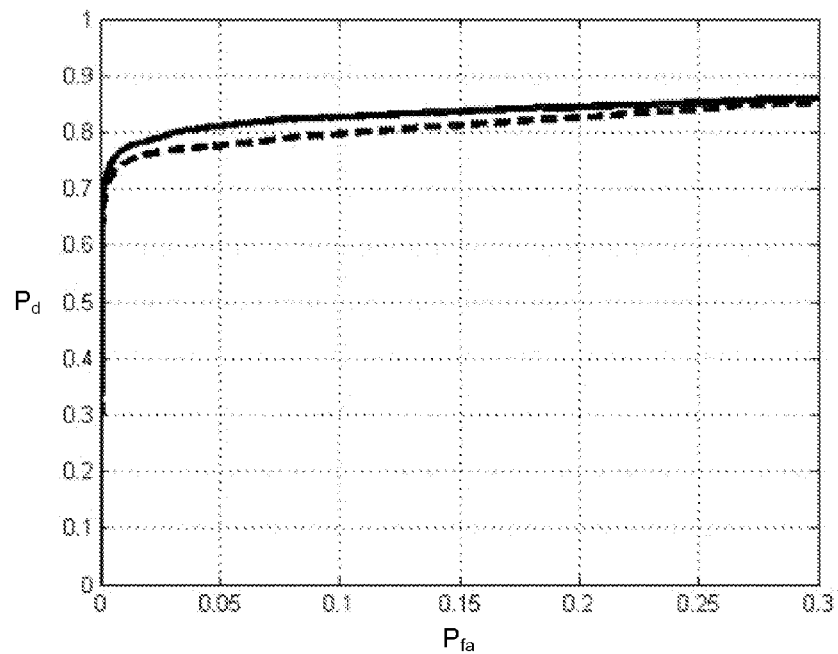
FIGS. 5A-5E illustrate same day receiver operating characteristic curves for different experimental activities according to various embodiments described herein.
Figure 5B:
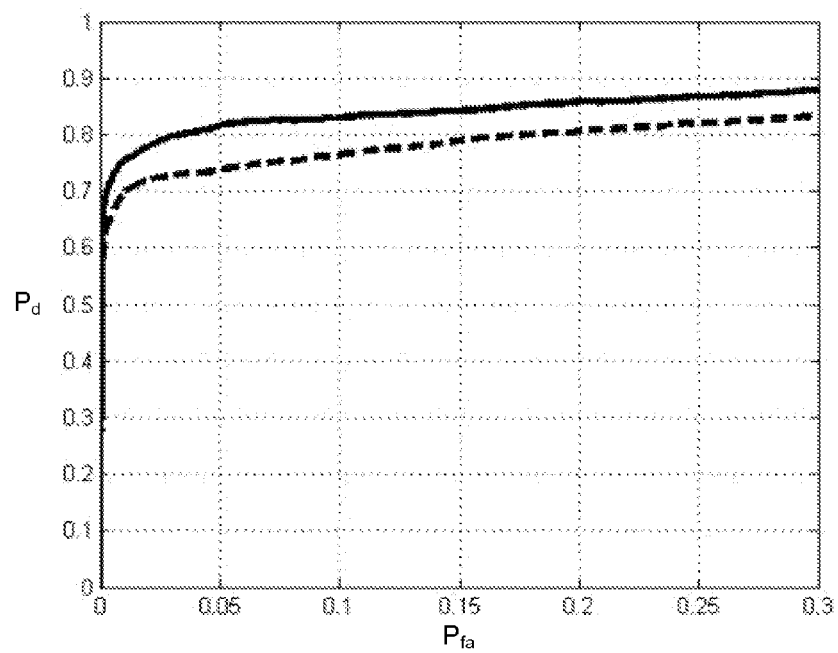
Figure 5C:
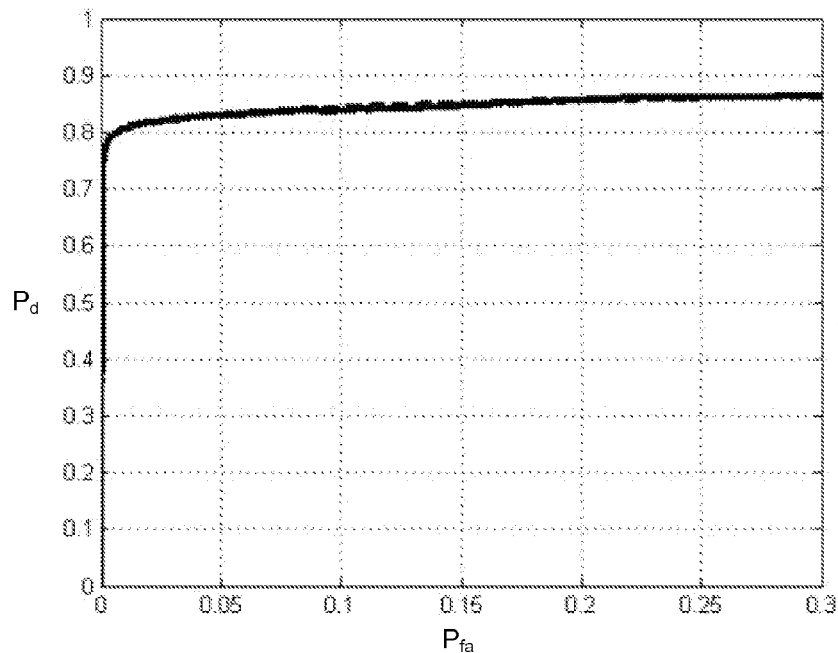
Figure 5D:
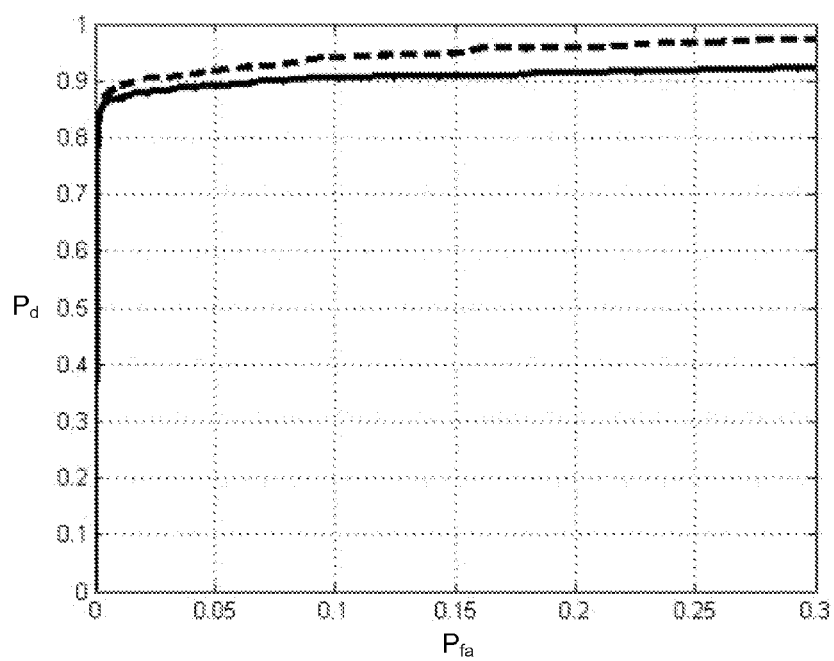
Figure 5E:
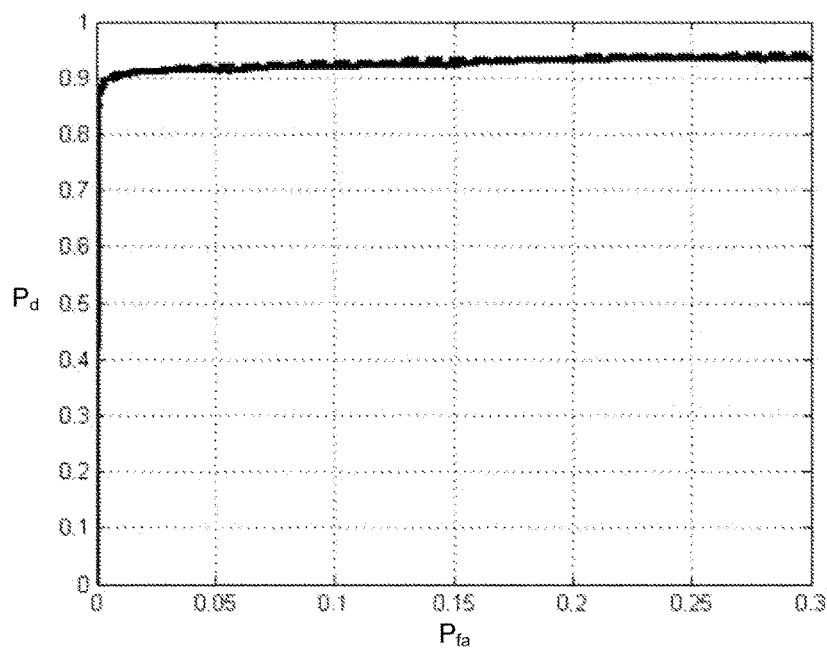
Figure 6A:
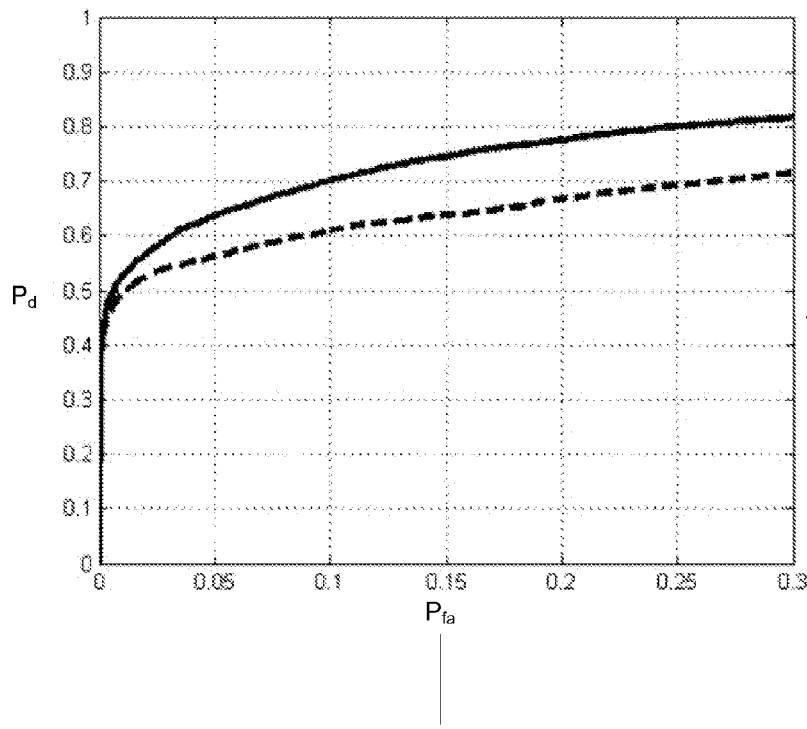
FIGS. 6A-6E illustrate different day receiver operating characteristic curves for different experimental activities according to various embodiments described herein.
Figure 6B:
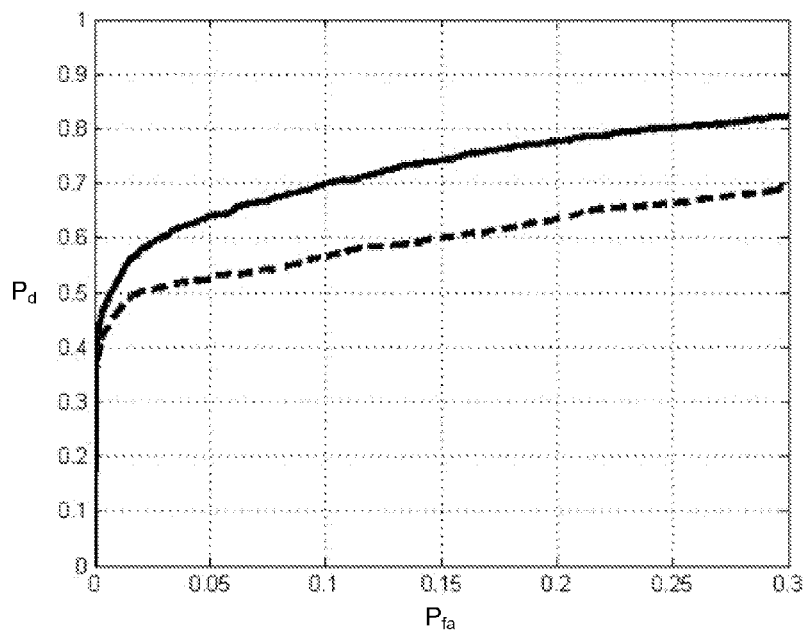
Figure 6C:
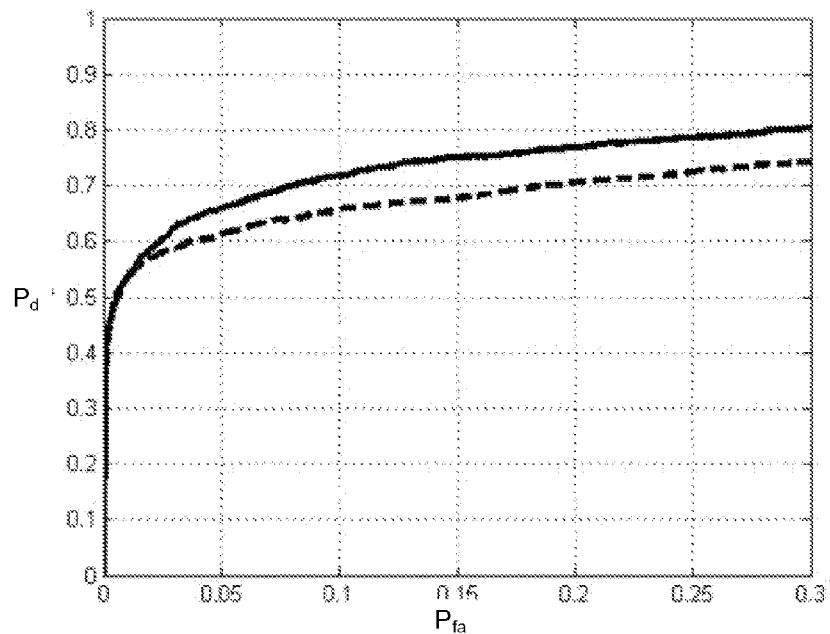
Figure 6D:
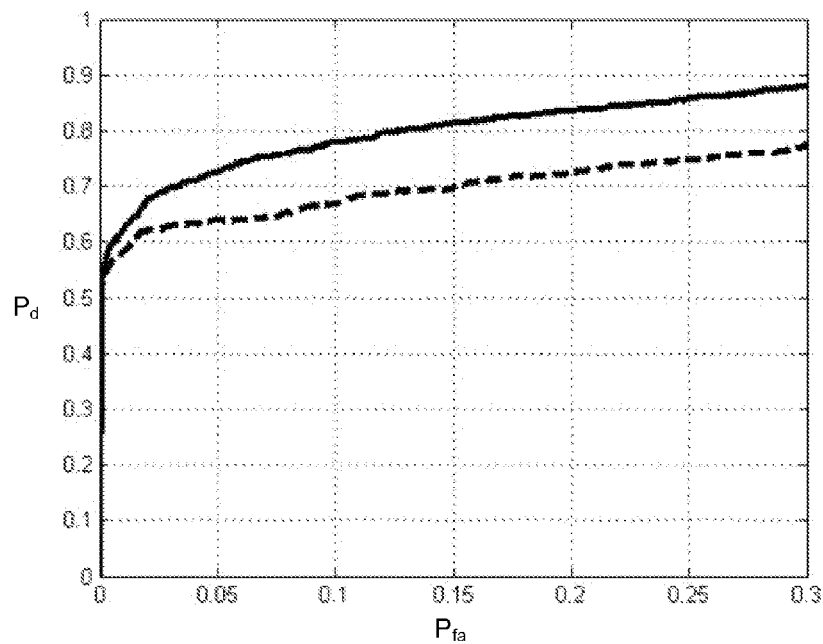
Figure 6E:
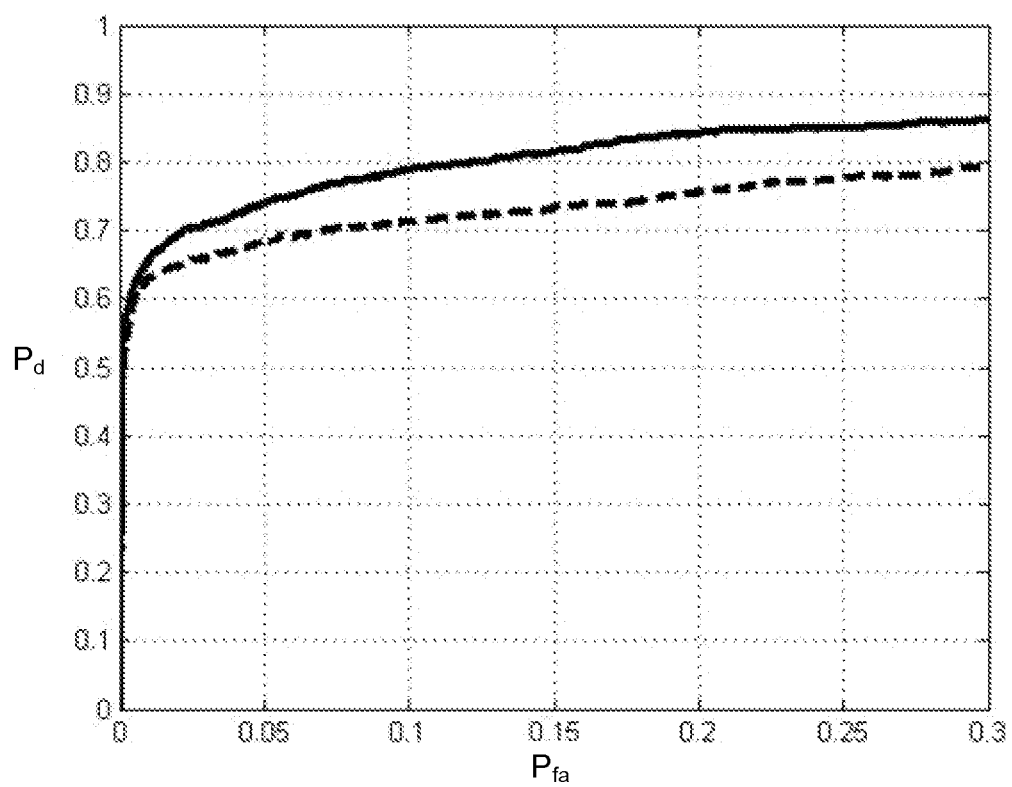

For each activity having a separate activity ID in Table 1, the subject walked three times around the loop shown in FIG. 4. The six activities are divided into two sets of three, where the phone's home location is the pocket or hip-pouch in the first set and the holster in the second set. Referring to FIG. 4, the portion of the data collected by the sensors over the first straight segment of the path for activities 13 and 16 was used reference or gallery data for identify authentication.

The passage of time between gallery or reference and current data collection is an important covariate in biometrics. This also implicitly includes covariates such as clothing, footwear, and mood. To study the performance of these covariates, data was collected twice for fifty-six of these subjects, with a few intervening days between collections. The first activity in each set is the subject walking around the loop three times at their natural pace. During the second activity in each set, the subject receives a phone call after the first loop, talks on the phone and returns the phone to its home location after hanging up. Similarly, during the third activity, the subject receives a text message, responds to it, and returns the phone to its home location. The data collection was started and stopped at the beginning and end of each activity.

The gender, age, and height statistics for the 101 subjects are shown in Table 2.

TABLE 2

Gender and Age of Subjects

| Gender | | Age (years) | | Height (cm) | |
|---|---|---|---|---|---|
| Female | 38 | 18 to 20 | 26 | 110 to 120 | 1 |
| Male | 63 | 21 to 30 | 58 | 151 to 160 | 16 |
| | | 31 to 50 | 10 | 161 to 170 | 33 |
| | | 51 to 64 | 6 | 171 to 180 | 34 |
| | | Unspecified | 1 | 181 to 200 | 17 |

The statistics of elapsed time between the two collections for each of the fifty-six subjects are shown in Table 3.

TABLE 3

Distribution of Elapsed Time Between Data Collection

| Time elapsed | # subjects |
|---|---|
| <1 week | 19 |
| ≤1 week and <2 weeks | 14 |
| ≤2 week and <3 weeks | 14 |
| ≤3 week and <8 weeks | 9 |

The data was organized into reference and probe data to arrive at five experiments to study algorithm performance under different conditions. The galleries always came from activities that involved no phone action (13 and/or 16) from the first session for the subject. The gallery corresponded approximately to the first straight segment of the walk for these activities as shown in FIG. 4. The probes were formed from the remaining walking portion of activities 13 and 16, and the walk-only parts of the remaining gait activities 14, 15, 17, and 18.

For same day evaluation, probes came from the first session (same as the reference or gallery data). For evaluation over more than one day, the probes came from the second session (different than the reference or gallery data). The probe portion of the data was split into five second segments to generate probes.

The five main experiments differed in which activities the gallery and probes came from. Experiment 1 (i.e., pocket, holster, walk, talk, text) was the most inclusive experiment, using activities 13 and 16 for gallery and activities 13 through 18 as probes. The probes were either from pocket-walks or holster-walks. Since the probes could come from either pocket or holster walk, the gallery is a concatenation of pocket and holster walk for each subject. Experiment 2 (i.e., pocket, walk, talk, text) was a pocket only experiment. The gallery is from activity 13. The probes are from activities 13, 14, and 15. Though all probes correspond to pocket-walks, only some are from the same activity as the gallery. Thus, this experiment involves taking the phone and replacing in the pocket between some probes and the gallery collection. Experiment 3 (i.e., holster, walk, talk, text) is a holster only experiment. The gallery is from activity 16. The probes are from activities 16, 17, and 18. Here again, the phone is removed and replaced in the holster between the gallery and some of the probes. Experiment 4 (i.e., pocket, walk) was a relatively restricted experiment using only pocket walk, activity 13. Both the gallery and probes are from activity 13. Here, the phone was not intentionally disturbed between the gallery and probe collection. Experiment 5 (i.e., holster, walk) was similar to experiment 4, with holster instead of pocket. Both the gallery and probes came from activity 16. In this case, the phone orientation is not expected to change between the gallery and probe collection.

All results for the PDA dataset are based on using both accelerometer and gyroscope data. The accelerometer and gyroscope vectors were concatenated into one vector of length six for each time instant. FIGS. 5A-5E show receiver operating characteristic (ROC) curves for all five experiments, respectively, on same day evaluations for the PDA dataset using the method described herein. In FIGS. 5A-5E, the solid lines represent ROC curves without probe data rotation/alignment, and the dashed lines represent ROC curves with probe data rotation/alignment. FIGS. 6A-6E show ROC curves for all five experiments, respectively, on different day evaluations for the PDA dataset using the method described herein. In FIGS. 6A-6E, the solid lines represent ROC curves without probe data rotation/alignment, and the dashed lines represent ROC curves with probe data rotation/alignment. In FIGS. 5A-5E and 6A-6E, Pd is probability of detection and Pfa is probability of false alarm.

Table 4 lists the equal error rates (EER), along with 95% confidence intervals, using the method described herein on the five experiments when run on the same day dataset.

TABLE 4

EER and 95% Confidence Intervals for Same Day Datasets

| | EER % ± 95% CI | |
|---|---|---|
| Experiment | No alignment | Rotation alignment |
| 1 Pocket, holster, walk, talk, text | 18.0 ± 1.0 | 16.1 ± 0.8 |
| 2 Pocket, walk, talk, text | 19.6 ± 1.6 | 15.7 ± 1.1 |
| 3 Holster, walk, talk, text | 15.1 ± 1.0 | 15.3 ± 0.9 |
| 4 Pocket, walk | 7.4 ± 0.2 | 9.4 ± 0.6 |
| 5 Holster, walk | 7.7 ± 0.7 | 8.0 ± 1.4 |

In experiments 4 and 5, the EER actually increased after rotation alignment. In these experiments, the alignment did less to increase the genuine similarity scores (e.g., the phone did not change orientation between gallery and probe for the same subject), but the impostor similarity scores increased due to alignment, making it harder to distinguish from genuine scores. Experiment 3, where the phone was in the holster, there was no significant change due to alignment, because the holster is typically placed in the same orientation (at least without a change in clothing, holster location, etc.). The most gain can be seen in experiment 2, where the phone was taken out and placed back in the pocket. While the EER without alignment for this experiment was higher than for experiment 3, due to the change in phone orientation, the alignment brought the EER to the same level in both experiments.

The no alignment results for experiment 1 (pocket and holster) are between those of experiments 2 (pocket) and 3 (holster), since it is a combination of galleries and probes in those experiments. With alignment, the EER is at almost the same levels as experiments 2 and 3.

Table 5 lists the EER and 95% confidence intervals using the method described herein on the five experiments when run on the different day dataset.

TABLE 5

EER and 95% Confidence Intervals for Different Day Datasets

| | EER % ± 95% CI | |
|---|---|---|
| Experiment | No alignment | Rotation alignment |
| 1 Pocket, Holster, walk, talk, text | 29.0 ± 0.6 | 21.5 ± 0.5 |
| 2 Pocket, walk, talk, text | 30.4 ± 0.0 | 21.5 ± 0.7 |
| 3 Holster, walk, talk, text | 26.8 ± 0.3 | 22.3 ± 0.1 |
| 4 Pocket, walk | 25.2 ± 0.9 | 17.5 ± 1.7 |
| 5 Holster, walk | 22.8 ± 1.7 | 17.1 ± 0.2 |

In these experiments, the probes were collected a few days later than the gallery. Without alignment, the results are understandably worse compared to the same day data. A part of the reason is that the clothing, energy-level, or the mood of the subject may have changed. Additionally, the device may have been placed in a different orientation due to a change of clothing. The rotation invariant algorithm described herein has been designed to address this issue. The benefit of aligning the probe in all five experiments can be clearly seen in Table 5. The EERs after alignment are about 70%-80% of the EERs before alignment. Again, the experiment that benefited the most is experiment 2, in which the phone was in the pocket. The smallest gains were for experiments 3 and 5, where the phone was in the holster, which restricts the possible orientation variations in the placement.

The McGill gait dataset, found at http://www.cs.mcgill.ca/~jfrank8/data/gait-dataset.html, and detailed in the article by J. Frank, S. Mannor, J. Pineau, and D. Precup, titled *Time series analysis using geometric template matching*, and published in IEEE Transactions on Pattern Analysis and Machine Intelligence, 35(3):740-754, 2013, is one publicly available dataset without restriction as to phone placement. The McGill dataset contains data from two sessions on two subjects. The sessions took place on different days. The sensor data contains total 3-D acceleration (includes gravity), but no gyroscope signals. The sensor rate was about 28 Hz. For evaluation of our algorithm on this dataset, we took the first 1500 samples (about 54 seconds) of the gait pattern as the gallery. The next 1500 samples (about 54 seconds) were taken to generate 5 second long probes. For same day evaluation, probes from the first session were compared against the gallery from first session and probes from the second session were compared against the gallery from the second day. For different day evaluation, probes were compared against the gallery from a different session. The results are presented in terms of identification accuracy in Table 6.

TABLE 6

Identification Accuracy

| | Identification accuracy | |
|---|---|---|
| Algorithm | Same day | Different day |
| Magnitude (baseline) | 67.5% | 32.5% |
| Inner product | 87.5% | 61.3% |
| Cosine similarity | 85.0% | 66.3% |
| Our method (no alignment) | 96.2% | 35.3% |

TABLE 6-continued

Identification Accuracy

| Algorithm | Identification accuracy | |
|---|---|---|
| | Same day | Different day |
| Our method (with alignment) | 96.5% | 67.5% |

The same day results (with and without alignment) using the method of orientation invariant gait matching are considerably better than that shown in other methods. Further, the different day results using the method of orientation invariant gait matching are also better than that shown in other methods.

The OU-ISIR inertial sensor gait dataset, described at http://www.am.sanken.osaka-u.acjp/BiometricDB/GaitL-P.html, has 3-D accelerometer and gyroscope data for two walks on 745 subjects. One of the walks is designated as the gallery and the other as the probe. The average length of the gallery is 5.97 seconds, and that of the probes is 4.85 seconds. Since the inertial sensor was placed in a fixed position at the back of the subject, very little rotation is expected between the gallery and probes. Due to this reason, it is not an ideal dataset for evaluating the benefits of the orientation invariant algorithm. However, the results show significant improvement.

TABLE 7

EER of Various Algorithms on OU-ISIR Data

| | EER % ± 95% CI | | |
|---|---|---|---|
| Algorithm | Accel. | Gyro. | Fused |
| Derawi | 14.3 | — | — |
| Rong | 14.3 | — | — |
| Gafurov | 15.8 | — | — |
| Yagi | — | 20.2 | — |
| Zhong Inner product | 8.9 | 11.3 | 7.1 |
| Zhong Cosine similarity | 6.8 | 10.9 | 5.6 |
| Our method (no alignment) | 6.6 ± 1.0 | 8.7 ± 1.6 | 6.3 ± 1.1 |
| Our method (with alignment) | 7.1 ± 1.9 | 9.6 ± 1.3 | 6.8 ± 1.5 |

The EERs slightly increase using rotation alignment, similar to same day experiments 4 and 5 in the PDA dataset. This is because, in the OU-ISIR dataset, the orientation of the sensors did not change between the gallery and probe data collections (just like experiments 4 and 5 in the PDA dataset). This results in a negligible increase in genuine similarity scores, but the impostor similarity scores increase more due to the alignment.

As described herein, a change in sensor orientation between gallery and probe data collection presents a serious problem in making inertial sensor based gait authentication a practical biometric. The orientation invariant gait matching system and method described herein provides a solution to this problem that can be easily implemented on mobile devices to work in real-time. The approach does not require any prior training or learning steps to estimate parameters or to build a model of the biometric. The results are better or comparable to the conventional methods as tested on different datasets.

Figure 7:
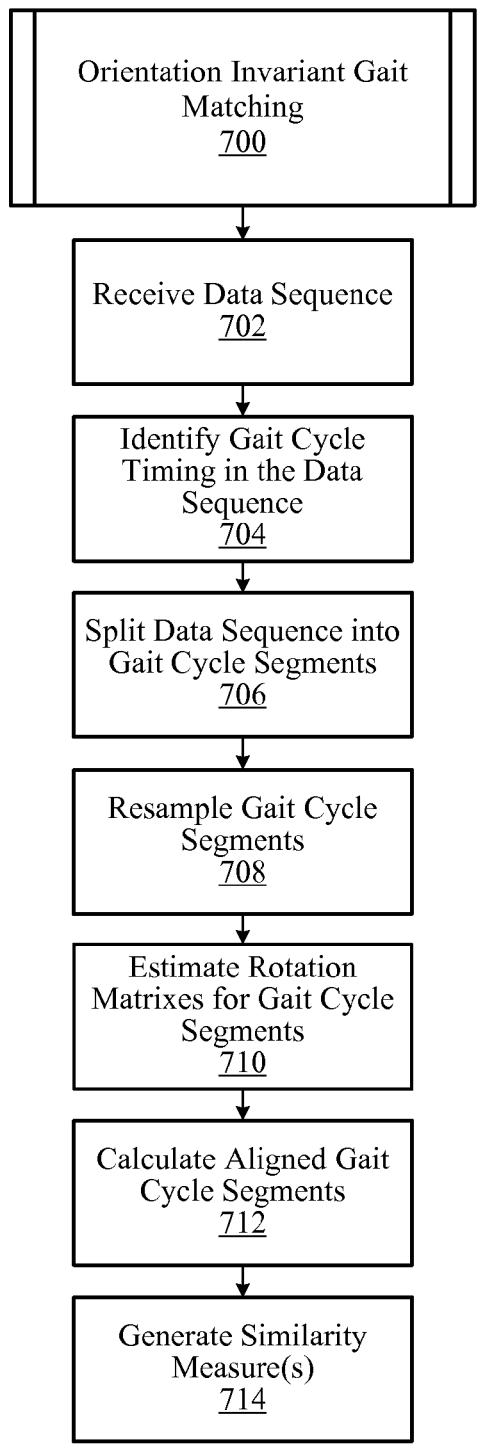
FIG. 7 illustrates a process of orientation invariant gait matching performed by the computing device shown in FIG. 1 according to an example embodiment described herein.

FIG. 7 illustrates a process 700 of orientation invariant gait matching performed by the computing device 100 shown in FIG. 1. In certain aspects, the process flowchart shown in FIG. 7 can be viewed as depicting an example set of steps performed by the computing device 100 according to one or more embodiments. The flowchart in FIG. 7 provides merely one example of a functional sequence or arrangement of steps that can be employed to implement the orientation invariant gait matching algorithm described herein. Although the process 700 is described below with reference to the computing device 100, other computing devices can perform the process 700.

At reference numeral 702, the process 700 includes the gait matching engine 130 receiving a data sequence from the sensors 110 (or, if previously stored, from the probe data sequences 124) in the computing device 100. As described above, the sensors 110 can capture and provide vector data sequences representative of the movement of the computing device 100 along a multi-axis coordinate system. In that context, a vector data sequence can include multiple, respective data sequences, each associated with or aligned to a geometric axis of the computing device 100.

At reference numeral 704, the process 700 includes the gait cycle segmenter 132 identifying a gait cycle timing in the data sequence received at reference numeral 702. To identify the gait cycle timing, the process can include the gait cycle segmenter 132 calculating an autocorrelation function of the data sequence, and detecting local maxima values and eliminating sub-dominant peak values of the autocorrelation function, as described above. Further, the process can include identifying a periodic timing between the local maxima values that is closest to one second as a gait cycle timing. At reference numeral 706, the process 700 includes the gait cycle segmenter 132 splitting the data sequence into a plurality of gait cycle segments based on the gait cycle timing identified at reference numeral 704.

At reference numeral 708, the process 700 includes the gait cycle segmenter 132 resampling one or more of the gait cycle segments into resampled gait cycle segments of fixed data sample length. Among the embodiments, each gait cycle segment can be resampled into a resampled gait cycle segment of fixed length m samples, where m can be any suitable number.

At reference numeral 710, the process 700 includes estimating, by the rotation matrix estimator 134, a rotation matrix for one or more of the resampled gait cycle segments. The estimation can be performed as described herein by minimizing a deviation between a given resampled gait cycle segment and a reference or gallery gait cycle segment. More particularly, in one embodiment, the estimation can be performed by minimizing a root mean squared deviation between the resampled gait cycle segment and the reference gait cycle segment using the Kabsch algorithm.

At reference numeral 712, the process 700 includes the similarity identifier 136 calculating an aligned gait cycle segment from the resampled gait cycle segment using the rotation matrix. In other words, for any resampled gait cycle segment for which a corresponding rotation matrix was estimated at reference numeral 710, the similarity identifier 136 can align the resampled gait cycle segment using the rotation matrix. The result of the process is similar to that described above with reference to FIG. 4.

At reference numeral 714, the process 700 includes the computing device 100 generating a similarity measure between the aligned gait cycle segment and the reference gait cycle segment. For example, reference gait cycle segment and the aligned gait cycle segment can be compared using the Tanimoto similarity measure as described above. For reference and aligned data segments that are similar, the value of this measure will be close to 1. The value will be less if they are dissimilar. Thus, the value of the similarity measure can be used for identity authentication, similar to the way that an individual's fingerprint can serve as a unique identifier. In some embodiments, the similarity measure can be compared against a threshold to make a final determination on identity authentication.

Figure 8:
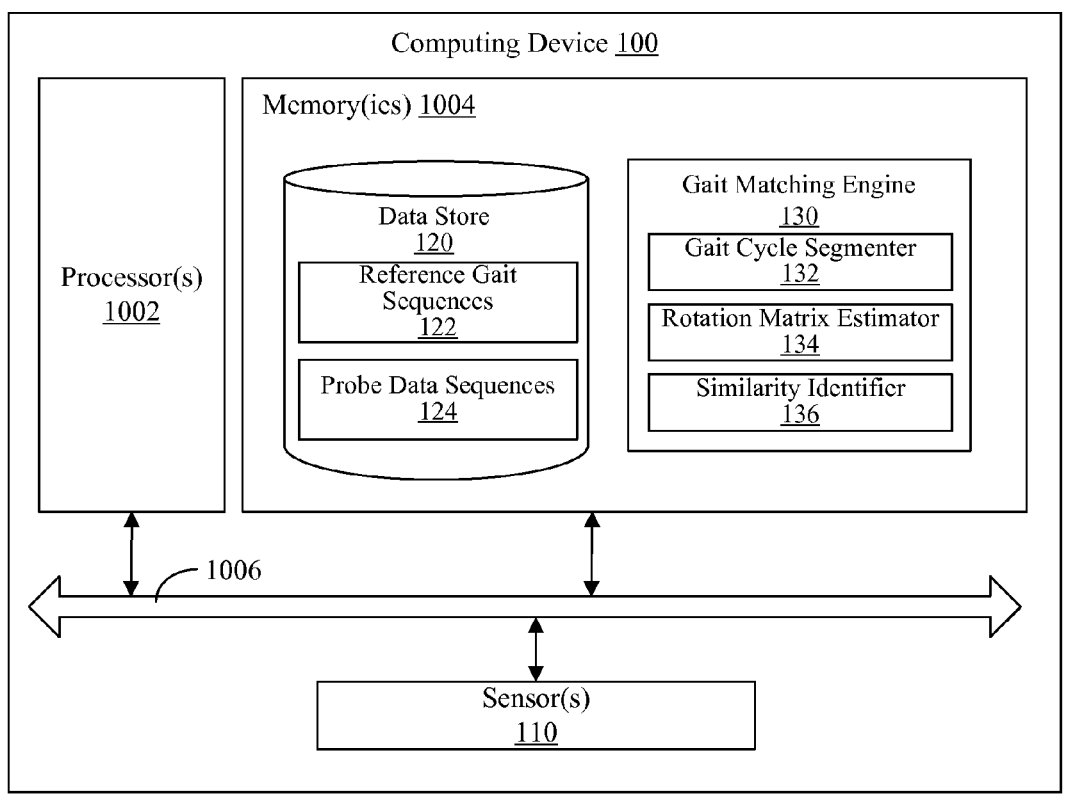
FIG. 8 illustrates an example schematic block diagram of the computing device shown in FIG. 1 according to various embodiments described herein.

FIG. 8 illustrates an example schematic block diagram of the computing device 100 shown in FIG. 1 according to various embodiments described herein. The computing device 100 includes at least one processing system, for example, having a processor 1002 and a memory 1004, both of which are electrically and communicatively coupled to a local interface 1006. The local interface 1006 can be embodied as a data bus with an accompanying address/control bus or other addressing, control, and/or command lines.

In various embodiments, the memory 1004 stores data and software or executable-code components executable by the processor 1002. For example, the memory 1004 can store executable-code components associated with the gait matching engine 130 for execution by the processor 1002. The memory 1004 can also store data such as that stored in the device data store 120, among other data.

It is noted that the memory 1004 can store other executable-code components for execution by the processor 1002. For example, an operating system can be stored in the memory 1004 for execution by the processor 1002. Where any component discussed herein is implemented in the form of software, any one of a number of programming languages can be employed such as, for example, C, C++, C#, Objective C, JAVA®, JAVASCRIPT®, Perl, PHP, VISUAL BASIC®, PYTHON®, RUBY, FLASH®, or other programming languages.

As discussed above, in various embodiments, the memory 1004 stores software for execution by the processor 1002. In this respect, the terms "executable" or "for execution" refer to software forms that can ultimately be run or executed by the processor 1002, whether in source, object, machine, or other form. Examples of executable programs include, for example, a compiled program that can be translated into a machine code format and loaded into a random access portion of the memory 1004 and executed by the processor 1002, source code that can be expressed in an object code format and loaded into a random access portion of the memory 1004 and executed by the processor 1002, or source code that can be interpreted by another executable program to generate instructions in a random access portion of the memory 1004 and executed by the processor 1002, etc.

An executable program can be stored in any portion or component of the memory 1004 including, for example, a random access memory (RAM), read-only memory (ROM), magnetic or other hard disk drive, solid-state, semiconductor, or similar drive, universal serial bus (USB) flash drive, memory card, optical disc (e.g., compact disc (CD) or digital versatile disc (DVD)), floppy disk, magnetic tape, or other memory component.

In various embodiments, the memory 1004 can include both volatile and nonvolatile memory and data storage components. Volatile components are those that do not retain data values upon loss of power. Nonvolatile components are those that retain data upon a loss of power. Thus, the memory 1004 can include, for example, a RAM, ROM, magnetic or other hard disk drive, solid-state, semiconductor, or similar drive, USB flash drive, memory card accessed via a memory card reader, floppy disk accessed via an associated floppy disk drive, optical disc accessed via an optical disc drive, magnetic tape accessed via an appropriate tape drive, and/or other memory component, or any combination thereof. In addition, the RAM can include, for example, a static random access memory (SRAM), dynamic random access memory (DRAM), or magnetic random access memory (MRAM), and/or other similar memory device. The ROM can include, for example, a programmable read-only memory (PROM), erasable programmable read-only memory (EPROM), electrically erasable programmable read-only memory (EEPROM), or other similar memory device.

The processor 1002 can be embodied as one or more processors 1002 and the memory 1004 can be embodied as one or more memories 1004 that operate in parallel, respectively, or in combination. Thus, the local interface 1006 facilitates communication between any two of the multiple processors 1002, between any processor 1002 and any of the memories 1004, or between any two of the memories 1004, etc. The local interface 1006 can include additional systems designed to coordinate this communication, including, for example, a load balancer that performs load balancing.

As discussed above, the gait matching engine 130 can be embodied, at least in part, by software or executable-code components for execution by general purpose hardware. Alternatively the same can be embodied in dedicated hardware or a combination of software, general, specific, and/or dedicated purpose hardware. If embodied in such hardware, each can be implemented as a circuit or state machine, for example, that employs any one of or a combination of a number of technologies. These technologies can include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc.

The flowchart or process diagram in FIG. 7 is representative of certain processes, functionality, and operations of the embodiments discussed herein. Each block can represent one or a combination of steps or executions in a process. Alternatively or additionally, each block can represent a module, segment, or portion of code that includes program instructions to implement the specified logical function(s). The program instructions can be embodied in the form of source code that includes human-readable statements written in a programming language or machine code that includes numerical instructions recognizable by a suitable execution system such as the processor 1002. The machine code can be converted from the source code, etc. Further, each block can represent, or be connected with, a circuit or a number of interconnected circuits to implement a certain logical function or process step.

Although the flowchart or process diagrams FIG. 7 illustrates a specific order, it is understood that the order can differ from that which is depicted. For example, an order of execution of two or more blocks can be scrambled relative to the order shown. Also, two or more blocks shown in succession in FIG. 7 can be executed concurrently or with partial concurrence. Further, in some embodiments, one or more of the blocks shown in FIG. 7 can be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any algorithm, method, process, or logic described herein that are embodied, at least in part, by software or executable-code components, can be embodied or stored in any tangible or non-transitory computer-readable medium or device for execution by an instruction execution system such as a general purpose processor. In this sense, the logic can be embodied as, for example, software or executable-code components that can be fetched from the computer-readable medium and executed by the instruction execution system. Thus, the instruction execution system can be directed by execution of the instructions to perform certain processes such as those illustrated in FIG. 7. In the context of the present disclosure, a "computer-readable medium" can be any tangible medium that can contain, store, or maintain any logic, application, software, or executable-code component described herein for use by or in connection with an instruction execution system.

The computer-readable medium can include any physical media such as, for example, magnetic, optical, or semiconductor media. More specific examples of suitable computer-readable media include, but are not limited to, magnetic tapes, magnetic floppy diskettes, magnetic hard drives, memory cards, solid-state drives, USB flash drives, or optical discs. Also, the computer-readable medium can include a RAM including, for example, an SRAM, DRAM, or MRAM. In addition, the computer-readable medium can include a ROM, a PROM, an EPROM, an EEPROM, or other similar memory device.

Disjunctive language, such as the phrase "at least one of X, Y, or Z," unless specifically stated otherwise, is to be understood with the context as used in general to present that an item, term, etc., can be either X, Y, or Z, or any combination thereof (e.g., X, Y, and/or Z). Thus, such disjunctive language is not generally intended to, and should not, imply that certain embodiments require at least one of X, at least one of Y, or at least one of Z to be each present.

It should be emphasized that the above-described embodiments of the present disclosure are merely possible examples of implementations set forth for a clear understanding of the principles of the disclosure. Many variations and modifications can be made to the above-described embodiment(s) without departing substantially from the spirit and principles of the disclosure. All such modifications and variations are intended to be included herein within the scope of this disclosure and protected by the following claims.

Therefore, at least the following is claimed:

1. A method of gait matching, comprising:
   receiving a data sequence from a sensor in a device;
   splitting the data sequence into a plurality of gait cycle segments;
   resampling a gait cycle segment among the plurality of gait cycle segments into a resampled gait cycle segment of fixed data sample length; and
   estimating, by at least one computing device, a rotation matrix for the resampled gait cycle segment by minimizing a deviation between the resampled gait cycle segment and a reference gait cycle segment.

2. The method of gait matching according to claim 1, further comprising:
   calculating an aligned gait cycle segment from the resampled gait cycle segment using the rotation matrix; and
   generating a similarity measure between the aligned gait cycle segment and the reference gait cycle segment.

3. The method of gait matching according to claim 1, wherein estimating the rotation matrix comprises minimizing a root mean squared deviation between the resampled gait cycle segment and the reference gait cycle segment using the Kabsch algorithm.

4. The method of gait matching according to claim 1, wherein the sensor comprises at least one of an accelerometer sensor or a gyroscope sensor.

5. The method of gait matching according to claim 1, wherein the data sequence comprises at least one of acceleration data or rate of rotation data experienced by the device along a plurality of dimensions.

6. The method of gait matching according to claim 1, wherein splitting the data sequence into a plurality of gait cycle segments comprises estimating a gait cycle timing of the data sequence using an autocorrelation function.

7. The method of gait matching according to claim 1, wherein splitting the data sequence into a plurality of gait cycle segments comprises:
   calculating an autocorrelation function of the data sequence;
   detecting local maxima values and eliminating sub-dominant peak values of the autocorrelation function;
   identifying a periodic timing between the local maxima values that is closest to one second as a gait cycle timing; and
   splitting the data sequence into the plurality of gait cycle segments using the gait cycle timing.

8. The method of gait matching according to claim 1, further comprising:
   resampling each of the plurality of gait cycle segments into a plurality of resampled gait cycle segments of the fixed data sample length; and
   estimating a rotation matrix for each of the plurality of resampled gait cycle segments.

9. The method of gait matching according to claim 8, wherein resampling each of the plurality of gait cycle segments comprises linearly interpolating each of the plurality of gait cycle segments into a fixed number of data samples.

10. A computing device, comprising:
    at least one inertial sensor; and
    a gait matching engine configured to:
      receive a data sequence from the at least one inertial sensor;
      split the data sequence into a plurality of gait cycle segments;
      resample a gait cycle segment among the plurality of gait cycle segments into a resampled gait cycle segment of fixed data sample length; and
      estimate a rotation matrix for the resampled gait cycle segment by minimizing a deviation between the resampled gait cycle segment and a reference gait cycle segment.

11. The computing device according to claim 10, wherein the gait matching engine is further configured to:
    calculate an aligned gait cycle segment from the resampled gait cycle segment using the rotation matrix; and
    generate a similarity measure between the aligned gait cycle segment and the reference gait cycle segment.

12. The computing device according to claim 10, wherein the inertial sensor comprises at least one of an accelerometer sensor or a gyroscope sensor.

13. The computing device according to claim 10, wherein the data sequence comprises at least one of acceleration data or rate of rotation data experienced by the device along a plurality of dimensions.

14. The computing device according to claim 10, wherein the gait matching engine is further configured to estimate a gait cycle timing of the data sequence using an autocorrelation function.

15. The computing device according to claim 10, wherein the gait matching engine is further configured to:
- calculate an autocorrelation function of the data sequence;
- detect local maxima values and eliminating sub-dominant peak values of the autocorrelation function;
- identify a periodic timing between the local maxima values that is closest to one second as a gait cycle timing; and
- split the data sequence into the plurality of gait cycle segments using the gait cycle timing.

16. The computing device according to claim 10, wherein the gait matching engine is further configured to:
- resample each of the plurality of gait cycle segments into a plurality of resampled gait cycle segments of the fixed data sample length; and
- estimate a rotation matrix for each of the plurality of resampled gait cycle segments.

17. The computing device according to claim 16, wherein the gait matching engine is further configured to linearly interpolate each of the plurality of gait cycle segments into a fixed number of data samples.

18. A method of gait matching, comprising:
- identifying a gait cycle timing in a data sequence captured by an inertial sensor;
- splitting the data sequence into at least one gait cycle segment based on the gait cycle timing;
- resampling the gait cycle segment into a resampled gait cycle segment of fixed data sample length;
- estimating, by at least one computing device, a rotation matrix for the resampled gait cycle segment by minimizing a root mean squared deviation between the resampled gait cycle segment and a reference gait cycle segment using the Kabsch algorithm;
- calculating an aligned gait cycle segment from the resampled gait cycle segment using the rotation matrix; and
- generating a similarity measure between the aligned gait cycle segment and the reference gait cycle segment.

19. The method of gait matching according to claim 18, wherein the data sequence comprises at least one of acceleration data or rate of rotation data experienced along a plurality of dimensions.

20. The method of gait matching according to claim 18, wherein splitting the data sequence into a plurality of gait cycle segments comprises:
- calculating an autocorrelation function of the data sequence;
- detecting local maxima values and eliminating sub-dominant peak values of the autocorrelation function;
- identifying a periodic timing between the local maxima values that is closest to one second as a gait cycle timing; and
- splitting the data sequence into the plurality of gait cycle segments using the gait cycle timing.

* * * * *